United States Patent [19]

Borek, Jr.

[11] Patent Number: 4,944,294

[45] Date of Patent: Jul. 31, 1990

[54] FACE MASK WITH INTEGRAL ANTI-GLARE, ANTI-FOG EYE SHIELD

[76] Inventor: Theodore S. Borek, Jr., 33 Allen Rd., Longmeadow, Mass. 01106

[21] Appl. No.: 183,783

[22] Filed: Apr. 20, 1988

[51] Int. Cl.⁵ .................... A62B 18/00; A62B 18/02; A61F 9/04

[52] U.S. Cl. .................. 128/206.19; 128/206.12; 128/201.15; 128/201.17

[58] Field of Search ............ 128/206.12, 206.13, 128/206.16, 206.19, 206.21, 206.23, 206.27, 206.28, 206.24, 201.12, 201.15, 201.17, 857, 863; 2/15, 427, 428, 431, 435, 8, 9, 12, 13, DIG. 7, 436; 52/171

[56] References Cited

U.S. PATENT DOCUMENTS

| | | | |
|---|---|---|---|
| 911,476 | 2/1909 | Cheesman | 128/206.12 |
| 2,056,753 | 10/1936 | Wagner | 128/206.19 |
| 2,280,055 | 4/1942 | Anderson | 2/435 |
| 2,280,482 | 4/1942 | Dreyfus | 2/435 |
| 2,353,978 | 7/1944 | Weber | 52/171 |
| 2,400,720 | 5/1946 | Staudinger | 52/171 |
| 2,665,686 | 1/1954 | Wood et al. | 2/435 |
| 4,014,047 | 3/1977 | Zobel | 128/206.19 |
| 4,464,797 | 8/1984 | Glassman | 128/206.19 |

FOREIGN PATENT DOCUMENTS

| | | | |
|---|---|---|---|
| 795771 | 3/1936 | France | 2/435 |
| 801619 | 8/1936 | France | 2/435 |

*Primary Examiner*—Edgar S. Burr
*Assistant Examiner*—Kiberly L. Asher

[57] ABSTRACT

A hospital face mask with an integral eye shield is disclosed. The shield prevents foreign bodies from entering a wearer's eyes, such as blood that spurts during surgery. It is made of an anti-glare, anti-fog material. In the preferred embodiment, the shield includes attached sponge strips that space it slightly away from the wearer's face, while still blocking sweat from dripping into the wearer's eyes.

2 Claims, 2 Drawing Sheets

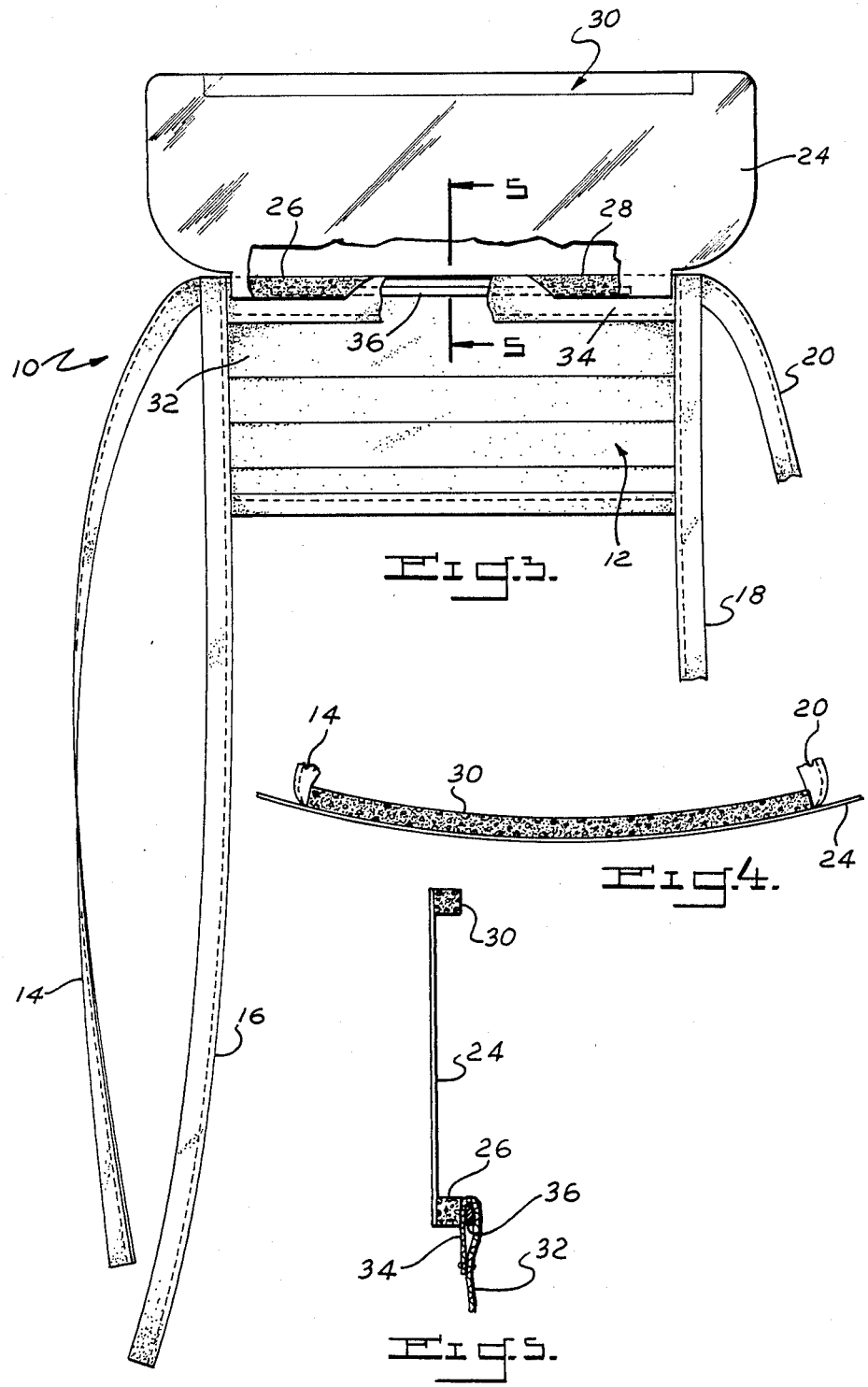

FACE MASK WITH INTEGRAL ANTI-GLARE, ANTI-FOG EYE SHIELD

BACKGROUND OF THE INVENTION

This application relates to a U.S. Design Patent Application which shows the present invention. That application was filed by the same Applicant on Mar. 24, 1988, and accorded Ser. No. 174,311.

The present invention relates to protective masks and more particularly to hospital face masks.

Face masks have been widely used in hospitals for decades. Among other things, they prevent germs from being transmitted between patients and staff.

Lately, however, both doctors and nurses have questioned the effectiveness of present masks. With the dramatic increase in cases involving A.I.D.S. (Acquired Immune Deficiency Syndrome), hospital members have been concerned with the possibility of catching this disease.

While the risk is minimal, they are nonetheless concerned about catching the disease through an inadvertent injection of a victim's body fluids into their own eyes. One way this could be achieved is through blood splattering during surgery.

In the past, there have been several masks that, at first glance, would appear to solve this problem. For example, U.S. Pat. No. 2,056,753 to Wagner shows a face mask with an integral plastic eye shield. While this prior mask might work, it has some definite drawbacks. Among other things, the shield can fog up or cause a glare from overhead lighting during surgery. Also, it has no way of preventing sweat from dropping into a wearer's eyes.

Accordingly, it is a primary object of the present invention to provide a unique face mask that overcomes the deficiencies of the prior art.

It is another general object to provide a face mask with an integral anti-glare, anti-fog eye shield.

It is a more particular object to provide such a mask with a sponge pad to catch the sweat from a wearer's forehead.

It is still a further object to provide a mask, commensurate with the above-listed objects, that is extremely simple and economical in design, yet extremely durable and safe to use.

The above and other objects and advantages of this invention will become more readily apparent when the following description is read in conjunction with the accompanying drawings.

BRIEF DESCRIPTION OF THE DRAWINGS

FIG. 3 is a front plan view of an unworn mask, with portions of the mask and its integral eye shield broken away for clarity and simplicity;

FIG. 4 is a top plan view of the FIG. 3 mask, showing a sponge that sits against a wearer's forehead, and with the mask's fastening straps broken away for simplicity; and FIG. 5 is a cross-sectional view of the mask, taken along line 5—5 of FIG. 3.

DETAILED DESCRIPTION OF THE PREFERRED EMBODIMENT

Figure 1:
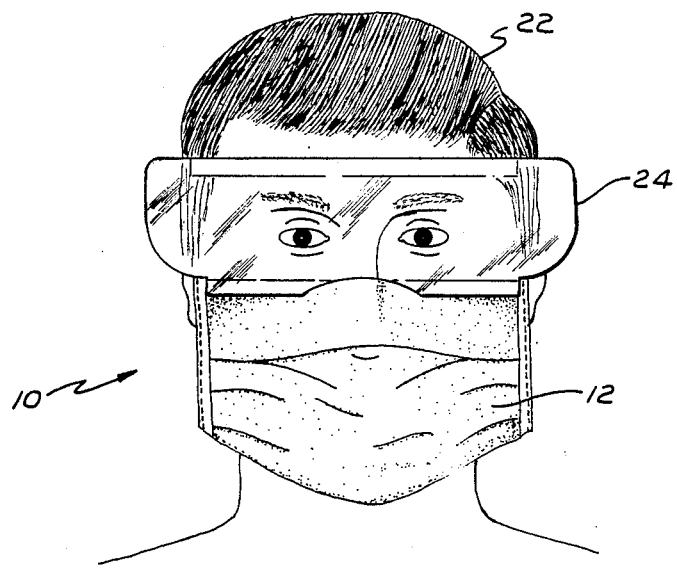
FIG. 1 is a front plan view of a person wearing a face mask which is constructed in accordance with the present invention.

Referring to the drawings in detail, the invention is shown and designated by the reference numeral 10. In its preferred embodiment, the invention 10 comprises a hospital face mask 12 that covers a wearer's mouth and nostrils; a plurality of tie straps (e.g., 14, 16, 18, 20) for attaching the mask onto a wearer 22; a unique anti-glare, anti-fog eye shield 24 that prevents foreign bodies from hitting the wearer's eyes; and a series of sponges 26, 28, 30 that, among other things, help the shield fit properly against the wearer.

The invention is marketed internationally under the trademark "SHIELDMATE" by IREMA U.S.A. Ltd. of Chicopee, MA. The face mask 12, which forms the bottom portion of invention 10, is preferably identical to the FACEMATE ® mask that already has been marketed successfully by IREMA. The FACEMATE ® mask 12 is constructed of a treated multi-ply fabric. The fabric is pleated so that the mask sits flat when stored, but can be spaced apart or opened up to accommodate the particular size and shape of a wearer.

The top pleat 32 of the FACEMATE ® mask includes a doubled-over stiched portion 34 with a pliable metal insert 36 (see FIG. 3). When bent, this strip 36 helps retain the shape of the opened mask and provides a gap for the wearer 22 to breathe through his nostrils.

Eye shield 24 is integrally attached to the mask's doubled-over portion 34 by any suitable means, such as glue. It is made of a transparent plastic—preferably an optic grade of polymer film—that has been coated with any suitable anti-fogging, anti-glare silicone agent, such as a dimethylsiloxane polymer.

In the illustrated embodiment, the shield 24 is shaped (for aesthetics) like a garden hoe. Instead of being directly glued onto the mask 12, two short sponge strips 26, 28 connect the shield to the mask.

To achieve this, the strips 26, 28 are first glued along the top edge of pleat 32, on opposite end portions of the doubled-over section 34. Then, the bottom of the shield is glued onto them.

Figure 2:
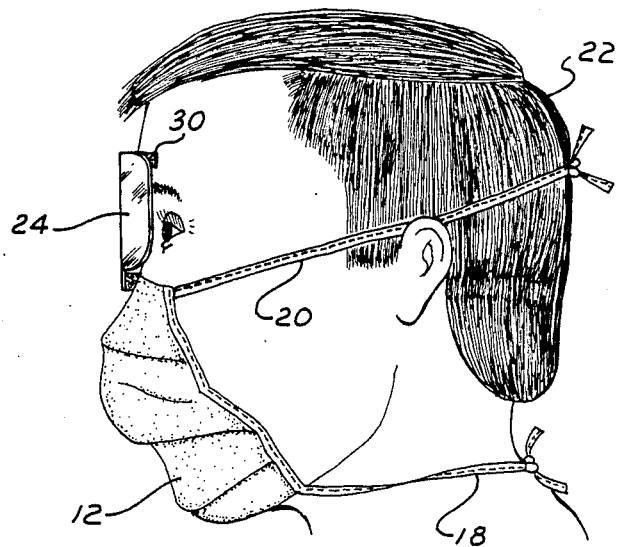
FIG. 2 is a side view of the wearer and mask shown in FIG. 1.

These strips 26, 28 combine with a longer upper strip 30 to space the eye shield 24 a slight distance apart from the wearer's face (see FIG. 2), whereby the shield 24 is laterally offset from the mask. Otherwise, the wearer's eyelashes would hit against the shield, causing an annoying discomfort.

Referring to FIGS. 1 and 4, the top sponge strip 30 is long enough to span the typical wearer's forehead. Since it is located at the base of the forehead, it captures sweat that might otherwise drip into the wearer's eyes.

It should be understood by those skilled in the art that obvious structural modifications could be made without departing from the spirit of the invention. For example, ear loops could be substituted for the tie straps 14, 16, 18, 20; or another face mask entirely could be substituted for the preferred FACEMATE ® mask 12. Accordingly, reference should be made primarily to the accompanying claims, rather than the foregoing specification, to determine the scope of the invention.

Having thus described the invention, what is claimed is:

1. A combined face mask and eye shield comprising:
   a. a non-woven mask adapted in size and shape to fit over the mouth and nostrils of a wearer, said mask having fastening means for attaching the mask onto a wearer's face;

b. a transparent eye shield connected at a bottom portion thereof to a top portion of the mask in a laterally offset manner by at least two sponge strips attached between the shield and mask, said sponge strips being spaced apart to provide a gap between the strips, shield and mask, wherein said shield is made of plastic that has been coated with an anti-fogging agent to prevent the wearer's breath from fogging up the shield when the mask is worn; and c. an upper sponge strip that is attached to a top portion of the shield, wherein said upper strip is adapted in size and shape to sit against and span the wearer's forehead when the mask is worn, whereby all the aforementioned sponge strips cooperate to space the shield sufficiently away from the wearer's face to prevent the wearer's eyelashes from contacting the shield, while positioning the upper strip to block sweat from dropping off the wearer's forehead into his eyes.

2. The combined mask and shield of claim 1 wherein the top portion of the mask includes a pliable metal insert to allow forming of the mask by pinching the insert.

* * * * *